US009861960B2

(12) United States Patent
Bai et al.

(10) Patent No.: US 9,861,960 B2
(45) Date of Patent: Jan. 9, 2018

(54) HYDROGENATION CATALYST, ITS METHOD OF PREPARATION AND USE

(71) Applicant: ExxonMobil Chemical Patents Inc., Baytown, TX (US)

(72) Inventors: Chuansheng Bai, Phillipsburg, NJ (US); Jean W. Beeckman, Columbia, MD (US); Adrienne J Thornburg, Columbus, OH (US); Natalie A. Fassbender, Nazareth, PA (US); Theodore E. Datz, Easton, PA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/916,707

(22) PCT Filed: Sep. 2, 2014

(86) PCT No.: PCT/US2014/053669
§ 371 (c)(1),
(2) Date: Mar. 4, 2016

(87) PCT Pub. No.: WO2015/057311
PCT Pub. Date: Apr. 23, 2015

(65) Prior Publication Data
US 2016/0193591 A1      Jul. 7, 2016

Related U.S. Application Data

(60) Provisional application No. 61/892,571, filed on Oct. 18, 2013.

(30) Foreign Application Priority Data

Dec. 17, 2013    (EP) .................................... 13197716

(51) Int. Cl.
*B01J 21/08*       (2006.01)
*B01J 23/38*       (2006.01)
(Continued)

(52) U.S. Cl.
CPC ............ *B01J 23/462* (2013.01); *B01J 23/42* (2013.01); *B01J 23/44* (2013.01); *B01J 23/464* (2013.01);
(Continued)

(58) Field of Classification Search
CPC ... B01J 21/08; B01J 23/38; B01J 23/42; B01J 23/44; B01J 23/46; B01J 23/462;
(Continued)

(56) References Cited

U.S. PATENT DOCUMENTS 3,986,947 A  *  10/1976  Wilson ..................... B01J 23/42
                                                    208/138
5,334,779 A      8/1994   Kuo
(Continued)

FOREIGN PATENT DOCUMENTS

EP          0 466 128       1/1992
EP          1 775 021       4/2007
(Continued)

*Primary Examiner* — Cam N. Nguyen
(74) *Attorney, Agent, or Firm* — Darryl M. Tyus (57) ABSTRACT

A method of preparing a hydrogenation catalyst, for example, a phthalate hydrogenation catalyst, comprising nebulizing a liquid containing a noble metal and a chelating agent comprising at least one nitrogen-containing functional group to form a nebulized liquid, and contacting the nebulized liquid with silica particles; a hydrogenation catalyst prepared by that method; and a method of hydrogenating unsaturated hydrocarbons, such as phthalates, in which an unsaturated hydrocarbon is contacted with hydrogen gas in the presence of the hydrogenation catalyst of the invention.

21 Claims, 1 Drawing Sheet

(51) Int. Cl.

| | | |
|---|---|---|
| *B01J 23/42* | (2006.01) | |
| *B01J 23/44* | (2006.01) | |
| *B01J 23/46* | (2006.01) | |
| *B01J 35/00* | (2006.01) | |
| *B01J 35/02* | (2006.01) | |
| *B01J 37/02* | (2006.01) | |
| *B01J 37/34* | (2006.01) | |
| *B01J 27/24* | (2006.01) | |
| *B01J 37/18* | (2006.01) | |
| *C07C 29/149* | (2006.01) | |
| *C07C 209/72* | (2006.01) | |
| *C07C 67/303* | (2006.01) | |
| *B01J 27/25* | (2006.01) | |
| *B01J 37/00* | (2006.01) | |

(52) U.S. Cl.
CPC ............ *B01J 27/24* (2013.01); *B01J 35/008* (2013.01); *B01J 35/023* (2013.01); *B01J 37/0213* (2013.01); *B01J 37/18* (2013.01); *B01J 37/343* (2013.01); *C07C 29/149* (2013.01); *C07C 67/303* (2013.01); *C07C 209/72* (2013.01); *B01J 21/08* (2013.01); *B01J 27/25* (2013.01); *B01J 37/0045* (2013.01); *B01J 2531/821* (2013.01)

(58) Field of Classification Search
CPC ........ B01J 35/008; B01J 35/023; B01J 37/34; B01J 37/0213; B01J 27/24
See application file for complete search history.

(56) References Cited

U.S. PATENT DOCUMENTS

| | | | |
|---|---|---|---|
| 5,422,329 A | 6/1995 | Wirtz et al. | |
| 5,498,590 A | 3/1996 | Burmeister et al. | |
| 5,622,908 A | 4/1997 | Abel et al. | |
| 5,936,126 A | 8/1999 | Rühl et al. | |
| 6,821,925 B2* | 11/2004 | Carruthers | B01J 21/04 502/335 |
| 2004/0034252 A1 | 2/2004 | Stochniol et al. | |
| 2005/0159310 A1* | 7/2005 | Ohno | B01D 53/945 502/439 |
| 2007/0072765 A1* | 3/2007 | Soled | B01J 37/0205 502/162 |
| 2011/0082311 A1 | 4/2011 | Soled et al. | |
| 2012/0271076 A1* | 10/2012 | Soled | B01J 23/468 585/252 |
| 2012/0289740 A1* | 11/2012 | Tan | B82Y 30/00 562/400 |
| 2012/0296111 A1 | 11/2012 | Königsmann et al. | |
| 2016/0193592 A1* | 7/2016 | Bai | B01J 37/0242 560/127 |
| 2016/0199814 A1* | 7/2016 | Bai | B01J 37/0242 560/127 |

FOREIGN PATENT DOCUMENTS

| | | |
|---|---|---|
| WO | 2004/045767 | 6/2004 |
| WO | 2004/046076 | 6/2004 |
| WO | 2004/046078 | 6/2004 |
| WO | 2013/165662 | 11/2013 |

* cited by examiner

HYDROGENATION CATALYST, ITS METHOD OF PREPARATION AND USE

PRIORITY CLAIM

Cross Reference to Related Applications

This application is a National Stage Application of International Application No. PCT/US2014/053669 filed Sep. 2, 2014, now expired, which claims the benefits of and priorities to U.S. Provisional Application Ser. No. 61/892,571 filed Oct. 18, 2013, and European Application No. 13197716.7, filed Dec. 17, 2013, now abandoned, the disclosures of each are fully incorporated herein by reference in their entireties.

FIELD OF THE INVENTION

The present invention relates to hydrogenation catalysts, in particular to methods for the preparation of noble metal catalysts, such as ruthenium (Ru) catalysts, for use in the hydrogenation of phthalates.

BACKGROUND

Plasticizers are incorporated into resins to increase their flexibility, workability, and dispensability. Phthalates, especially, the high molecular weight phthalates (HMWP), are used as plasticizers in PVC. Alternative to phthalates are desirable due to environmental, legislative and regulatory concerns. In particular, the uses of phthalates as plasticizers are under severe pressure. Hydrogenation of phthalates produces 1,2-cyclohexyl dicarboxylates, hereinafter also referred to as cyclohexanoates, which can also be used as plasticizers.

Previous research showed that catalysts consisting of noble metals supported on alumina ($Al_2O_3$) with low surface areas are active for the hydrogenation of phthalate to cyclohexanoates. U.S. Pat. No. 5,936,126 (BASF) discloses the hydrogenation of phthalates to cyclohexyl dicarboxylates using catalysts consisting of Ru supported on low surface area alumina at 80° C. to 120° C. and under 10-20 MPa (100-200 atmospheres) pressure.

It has also recently been discovered that materials consisting of noble metals, such as Ru, supported on a silica ($SiO_2$) support with "remnant structure" produced by deposition of an organic ruthenium compound on a silica support to form an organic ruthenium complex on or in the support, followed by decomposition of the complex, have much higher activities and stabilities in the phthalate hydrogenation than reported Ru/$Al_2O_3$ catalysts. WO 2004/046076, WO 2004/045767 and WO 2004/046078 (ExxonMobil) disclose catalysts of Ru on silica supports prepared with the remnant structures. However, diffusion rates of bulky reactants such as phthalates through catalysts are slow with most of the chemical reactions taking place on the surface of the catalyst. Accordingly, only a proportion of the ruthenium deposited on a porous silica support is at effective catalytic sites, with metal sites in the center of the support making little contribution.

It is known to produce catalysts that have a shell or rim structure in which particles of support material are provided with noble metal coatings, also called "shell" catalytic materials. For example, U.S. Pat. No. 5,422,329 (Hoechst) discloses a supported catalyst for the production of vinyl acetate from acetic acid, ethylene and oxygen, prepared by impregnating particles of a silica support with an atomized solution of palladium and other noble metal salts to coat the particles. U.S. Pat. No. 5,622,908 (Hoechst) discloses similar catalysts prepared by spraying the support particles with an atomized solution of the noble metal salts. U.S. Pat. No. 5,498,590 (Degussa) also discloses the preparation of a fixed bed catalyst support for vinyl acetate synthesis, in which pyrogenic silica support is sprayed with an atomized impregnating solution comprising a precursor of a noble metal catalytic component to form a shell coating. EP 1 775 021 (Honda) discloses a method of producing catalysts for cleaning emissions from internal combustion engines in which catalyst nanoparticles are deposited on a porous filter support.

Evenly dispersing noble metals onto the surface of silica particles has been found to be problematic using common dispersion techniques. Typically, multiple coating steps are needed to fully coat the surface, and substantial quantities of the noble metals penetrate into the body of the support material where they are inaccessible to the phthalate molecules and are thus unavailable for catalyzing phthalate hydrogenation. US 2012/0296111 (BASF) discloses an egg-shell catalyst for hydrogenating carbocyclic aromatic compounds, such as phthalates, comprising a noble metal, such as ruthenium, deposited on a silica support material. The silica support is in the form of shaped bodies of from 0.5 mm to 25 mm, such as in the form of spherical particles of 1.0 mm to 6.0 mm in diameter. At least 90% of the pores present in the catalyst have a pore size of from 6 to 12 nm. The catalyst is prepared by impregnating a solution of a noble metal salt, such as ruthenium acetate, and an organic acid dispersion aid onto the silica support, for example, by spraying. The ruthenium in the egg-shell catalyst is described as being present down to a penetration depth of 200 μm and the metal dispersity is described as being from 30% to 60% as measured using DIN 66136. Despite the use of repeated impregnation steps to disperse the ruthenium onto the surface of the silica support material, it has been found that the metal is not well dispersed in the catalyst prepared by the method of US 2012/0296111, resulting in a low benzene hydrogenation activity (BHA).

As a consequence, there remains a need for improved metal oxide-supported noble metal catalysts which are highly active in hydrogenation of aromatic compounds, in particular, that allow rapid conversion of phthalates to cyclohexane carboxylic acids and carboxylates. In particular, there is a need for a hydrogenation catalyst that can both facilitate the mass transfer of large aromatic molecules, such as phthalates, during catalytic reactions and make efficient use of the expensive noble metals. There also remains a need for a more efficient method of dispersing a noble metal, salt such as ruthenium, onto the surface of a silica support, especially a small particle size silica support.

SUMMARY OF THE INVENTION

The present inventors have found that when a fine mist of droplets of a liquid containing a noble metal and a chelating agent, for example prepared using ultrasonic nebulization, is deposited onto a silica support, e.g., by spraying, the noble metal can be dispersed evenly across the surface of the support with very little penetration into the interior of the support. As a result, an egg shell or rim structure silica-supported noble metal catalyst that has a high catalytic activity can be produced in an efficient manner.

In a first aspect, the invention provides a method for the preparation of a silica-supported noble metal catalyst, in particular a silica-supported ruthenium catalyst, in which a liquid containing a noble metal, preferably ruthenium, and a chelating agent, is nebulized and deposited onto particles of a silica support. In one embodiment, the invention provides a method for the preparation of a silica-supported noble metal (e.g., ruthenium) hydrogenation catalyst comprising the steps of: (a) nebulizing a liquid containing a noble metal and a chelating agent wherein the chelating agent comprises at least one nitrogen-containing functional group selected from the group consisting of amine and imine functional groups; and (b) contacting the nebulized liquid of step (a) with silica support particles, e.g., by spraying the nebulized liquid onto the silica particles, to produce a noble metal-containing silica support. The silica particles used as silica support in step (b) preferably consist of silica particles having an average diameter of about 2.4 mm or less, such as an average diameter of from about 0.7 mm to about 2.4 mm. The noble metal-containing silica support obtained in step (b) may be used as such as hydrogenation catalyst or it may be subjected to further processing steps before being used as a catalyst. The method of the first aspect of the invention thus optionally further comprises the step of drying; and/or (c) calcining the noble metal-containing silica support prepared in step (b). The calcining step (c) is advantageously performed subsequent to the optional drying step. The method, optionally further, comprises the step (d) of activating the catalyst for instance by contacting the noble metal-containing silica support obtained in step (b) or (c) with hydrogen gas to form an activated catalyst.

In a second aspect, the invention provides a silica-supported noble metal catalyst obtainable by the method of the first aspect of the invention. In a particular embodiment, the second aspect of the present invention provides a silica-supported noble metal, especially ruthenium, catalyst comprising a noble metal (e.g., ruthenium) deposited onto a silica support wherein the silica support consists of silica particles having an average diameter of from about 0.7 mm to about 2.4 mm. Said silica-supported noble metal catalyst typically comprises from about 0.2 wt % to about 1 wt % of noble metal. Advantageously, in the catalyst of the second aspect of the present invention, the median radial penetration of the noble metal into the silica support is no more than about 40% of the average diameter of said silica support. Still advantageously, the silica-supported noble metal catalyst of the second aspect of the present invention has a hydrogen to noble metal chemisorption ratio of at least about 0.50, especially at least about 0.60. Advantageously, the median pore size of the catalyst is at least 12 nm, for example at least 13 nm and especially at least 15 nm. The hydrogenation catalysts of the invention are suitable for the catalysis of hydrogenation processes, for example, processes in which unsaturated hydrocarbons, such as aromatic compounds, are hydrogenated using hydrogen gas, especially for use in phthalate hydrogenation processes.

In a third aspect, the invention provides a method of hydrogenating an unsaturated hydrocarbon, such as a phthalate, comprising the step of contacting the unsaturated hydrocarbon with a catalyst of the second aspect of the invention or a catalyst obtainable or obtained by the method of the first aspect of the invention, for example, in the presence of hydrogen gas.

It has been found that the method of the first aspect of the invention, in which the silica support is bombarded with very small droplets of a liquid containing a noble metal, especially ruthenium, and a chelating agent that is an organic compound comprising at least one nitrogen-containing functional group selected from the group consisting of amine and imine functional groups, leads to an even dispersion of the metal on the surface of the silica support particles, even on very small silica support particles. For example, the method has been found to be particularly useful in preparing catalyst with silica particles having an average diameter of about 2.4 mm or less. This is especially advantageous as catalysts with a small particle size have the advantage of packing densely in a reactor. Furthermore, the method of the invention has been found to provide a catalyst with an efficient catalyst loading, with the relatively small amounts of noble metal present being distributed onto the surface of the support material with little penetration of the noble metal into the interior of the silica particles. Accordingly, the catalyst produced by the method of the invention has been found to have a high activity for the hydrogenation of unsaturated hydrocarbon compounds, in particular, for the hydrogenation of phthalates. Without being bound by any theory, it is believed that the catalysts prepared by the method of the invention are especially suitable for the hydrogenation of phthalates because said phthalates do not penetrate into the body of the support material so that a reduced loading of expensive metal is required to achieve the same activity as that which would be required if the metal were deposited throughout the catalyst particles. What is more, it has also been found that the catalyst particles of the invention are evenly coated with a highly dispersed noble metal in a single step process without the need for multiple impregnation steps. Thus, the method of the invention is an efficient way of producing a hydrogenation catalyst, which is both highly active in phthalate hydrogenation, having a high active surface area per unit volume or per unit mass of catalyst material, and which can at the same time be packed densely in a reactor, i.e., which has a small particle size.

DETAILED DESCRIPTION OF THE INVENTION

The noble metal present in the catalyst of the present invention is selected from the group consisting of ruthenium, rhodium, palladium, platinum, and mixtures thereof, preferably ruthenium, most preferably ruthenium as the sole active metal.

The silica support particles used in the method of the first aspect of the invention can have any suitable shape or form. Preferably, the silica support particles are in the form of tablets, pellets, extrudates, spheres, beads and the like and combinations thereof. The extrudates may be of any cross section, for example, circular to form cylinders or tubes as well as trilobe or quadrulobe to form prisms. The silica support particles are typically silica extrudates or silica beads, preferably silica beads.

If the silica support particles used in the method of the first aspect of the present invention are in the form of silica beads, spheres, tablets or pellets, the particle size distribution of said silica support may be determined by dry sieve analysis according to ASTM C136-96a. Said particle size distribution may be characterized by its D10, D50 and D90 values where D50 corresponds to the size at which 50 wt % of the sample is smaller and 50 wt % of the sample is larger. In the present invention, D50 is used to characterize the silica support average particle size or average diameter. The width or span of the particle size distribution is calculated as (D90-D10)/D50. The particle size distribution of a population of particles used in the present invention is typically relatively narrow, for instance, with a span equal to or lower than 2, preferably equal to or lower than 1.5, more preferably equal to or lower than 1, in particular equal to or lower than 0.5 such as about 0.2.

If the silica support particles used in the method of the first aspect of the present invention are the form of extrudates, i.e., in the form of elongated shapes having a substantially constant cross section which corresponds to the hole of the extrusion die, the silica support particles may be characterized by an average length, an average diameter and an average aspect ratio. According to the present invention, the length of an extrudate corresponds to the extruded length of said extrudates, the diameter of an extrudate corresponds to the outside diameter of said extrudate cross section, i.e., the diameter of the smallest circle circumscribing the cross section, and the aspect ratio of an extrudate corresponds to the ratio of its length on its diameter. Thus, for example, for a cylindrical extrudate, the diameter of the particle corresponds to the diameter of the disc cross section. For an extrudate having an elliptic cross section, the diameter of the particle is the major axis of the ellipse, i.e., the line segment that runs through the center and both foci, with ends at the widest points of the extruded elliptical cross section. For a symmetric quadrulobe extrudate, the diameter is the highest dimension of the quadrulobe section, i.e., the longest distance, in a straight line between two points on the quadrulobe cross section and its center. The diameter of an extrudate is substantially constant, as the cross section of the extrudate is dictated by the size of the hole in the extrusion die. The average length, average diameter, and average aspect ratio of the extrudate silica support particles of the present invention may be determined by optical scanner imaging using ALIAS Image Analysis System (Cascade Data System). The sample size is typically of 150 to 250 particles, without sample preparation per se. The average length and average diameter are the numerical averages (arithmetic means) of the measured individual lengths and diameters while the aspect ratio is the fraction of said average length on said average diameter. The average length of the extrudate silica support particles used in the method of the first aspect of the invention can vary widely and is not critical. In the present invention, the average length to diameter aspect ratio of said extrudate silica support particles is usually at least 1, most often higher than 1, typically at least about 2, in particular at least about 2.5, for example, at least about 3. Said average aspect ratio is usually at most about 10, typically at most about 8, for instance, at most about 5.

The average diameter of the silica support particles used in the method of the first aspect of the invention, whether beads, spheres, tablets or pellets, extrudates or other forms, is generally of no more than about 2.4 mm, for example, no more than about 2.2 mm, especially no more than about 2.0 mm. In some embodiments, the silica support consists of particles having an average diameter of less than about 2.0 mm, for example, no more than about 1.8 mm, especially no more than about 1.7 mm. Typically, the particles have an average diameter of at least 0.7 mm. Preferably, the silica support consists of particles having an average diameter of from about 0.8 mm to about 2.2 mm, especially from about 1.0 mm to about 2.0 mm, for example, from about 1.2 mm to about 1.8 mm. The catalyst of the second aspect of the invention is typically of substantially the same size as the silica support listed above. For example, a catalyst of the second aspect of the invention based on silica support particles in the form of beads, spheres, tablets, pellets or extrudates, preferably consists of particles having an average diameter of from about 0.7 mm to about 2.4 mm, especially from about 0.8 mm to about 2.2 mm, for example, from about 1.0 mm to about 2.0 mm. The average diameter of the particles of support or catalyst may, for example, be measured by dry sieve analysis and/or optical scanner imaging as appropriate.

The silica support particles used in the method of the invention preferably has a silica content of at least 60 wt %, for example at least 80 wt %. In addition to silica, the silica support particles may, for example, also comprise alumina, however alumina is preferably a minor component. Accordingly, the silica support particles preferably comprise no more than 40 wt % alumina, for example, no more than 20 wt % alumina, especially no more than 10 wt % alumina.

The silica support particles used in the method of the invention typically has a pore volume of at least about 0.2 ml/g, for example, at least about 0.5 ml/g, especially at least about 0.6 ml/g. The silica support particles typically have a pore volume of no more than about 3.0 ml/g, for example, no more than about 2.0 ml/g, especially no more than about 1.5 ml/g. For example the silica support particles typically have a pore volume in the range of from about 0.4 ml/g to about 1.5 ml/g, such as from about 0.6 to about 1.3 ml/g or to about 1.2 ml/g. The pore volume may be determined by mercury porosimetry, for example, according to ASTM D4284-12. Silica support particles for use in the present invention generally have a surface area, measured by the Brunauer, Emmett, Teller (BET) method, in the range of from about 20 $m^2/g$ to about 400 $m^2/g$, preferably in the range of from about 40 $m^2/g$ to about 300 $m^2/g$, and more preferably in the range of from about 50 $m^2/g$ to about 200 $m^2/g$.

The silica support particles used in the present invention typically have a median pore size of at least about 8 nm, for example at least about 10 nm. Advantageously, the median pore size of the catalyst is at least 12 nm, for example, at least 13 nm and especially at least 15 nm. The silica support particles used in the present invention preferably have a median pore size of no more than about 300 nm, for example, no more than about 200 nm, especially no more than about 150 nm. For example, the silica support particles may have a median pore size of from about 10 to about 100 nm, such as from about 15 nm to about 80 nm. The median pore size may be determined by mercury porosimetry, for example, according to ASTM D4284-12. The pores may be approximately spherical or have an irregular shape. The pore size is the largest dimension of the pore, which is also known in the art as the "pore diameter" or "pore axis". It has been found that silica supports having relatively large pore sizes, such as a median pore size of 10 nm or more, especially 13 nm or more, can facilitate the mass transfer of large molecules of phthalate during catalytic reactions, which can be beneficial to the catalyst activity for phthalate hydrogenation to cyclohexanoates. Typically, the silica support particles have a crush strength of at least 800 g/mm, for example, at least 1000 g/mm, preferably at least 1200 g/mm. Crush strength is measured using the standard test method for single pellet crush strength of formed catalyst shapes set out in ASTM D4179-01. Suitable silica support particles having the properties described above are described in U.S. Pat. No. 8,216,958 (ExxonMobil), the disclosure of which is incorporated herein by reference.

Deposition of the noble metal onto the surface of the silica support particles can be achieved by any suitable method allowing contacting of the nebulized liquid containing the noble metal and the chelating agent with the silica support particles, typically by spraying the nebulized liquid containing the noble metal and the chelating agent onto the silica support particles. In the present invention, the expression "nebulizing a liquid" means converting said liquid into a mist or fine spray. The term "nebulizing" is considered to be equivalent to the term "atomizing" in the context of the present invention. Typically, the nebulized droplets have an average (arithmetic mean) diameter of from about 1 μm to about 50 μm, for example, from about 2 μm to about 40 μm, especially from about 3 μm to about 35 μm, such as from about 5 μm to about 35 μm. The liquid can be nebulized using any nebulizer (or atomizer) available in the art, provided that it ensures a constant narrow droplet size distribution, whereby at least 60%, preferably at least 80% of the entire volumetric flow should be atomized into droplets with diameters which are not greater than double the average arithmetical droplet diameter. This is advantageous as it prevents non-uniform impregnation of the surface of the silica support particles. In a preferred embodiment, the liquid is nebulized in an ultrasonic nebulizer that employs ultrasonic waves to provide a vapor mist, and is contacted with the silica support via nozzles. The nebulized liquid can be contacted with the silica support particles at any suitable temperature, typically at a temperature of at least 10° C. below its boiling point, for instance at room temperature. The nebulized liquid can be contacted with the silica support particles with or without pressure and with or without support gas, preferably without pressure and without support gas.

Advantageously, the volume of liquid deposited on the silica support particles is no more than 40%, preferably no more than 35%, especially no more than 30% of the solvent absorption capacity of said silica support particles. Typically, a volume of liquid that is from about 15% to about 40%, for example, from about 20% to about 35%, especially from about 24% to about 30% of the solvent absorption capacity of the silica support particles is deposited on the silica support in step (b). The solvent absorption capacity of the silica support depends on the respective solvent/support material combination. The solvent absorption capacity for a specific solvent/support combination can be determined in a simple way by putting the support material in a glass filled with the solvent at room temperature to absorb solvent until no more air bubbles rise. The support material is then removed from the solvent, its surface is dried with paper and it is weighed. The quantity of absorbed solvent, and thus the sought solvent absorption capacity, is determined from the difference in weights of the support material before and after the absorption of solvent. The degree of penetration of the noble metal into the silica support is linked to the amount of liquid deposited onto the silica support. The median radial penetration of the noble metal into the silica support particles is advantageously no more than 40% of the average diameter of the silica support particles, preferably no more than 30%, especially no more than 20%, for example, no more than 15%, such as no more than 12% of the average diameter of the silica support particles. In an especially preferred embodiment, the deposition of the noble metal onto the silica support particles in the method of the present invention results in a median radial penetration of approximately 10% of the average diameter of the silica support particles. The radial penetration of the noble metal into the silica support can be measured from an optical microscopy image of a cross section of the silica-supported noble metal catalyst particles. In the case of silica beads used as a support, the total volume of a silica bead is calculated as $V=(4/3)\pi r^3$, where r is the radius of a silica sphere. Thus, for a radial penetration of 10%, the inner volume of the silica bead without noble metal deposition is: $(4/3)\pi(0.9r)^3=(0.9)^3 V=0.729V$ and the volume of the noble metal shell coating is $\Delta V\%=(V-0.729V)=0.271V$. Thus, for silica support particles in the form of spheres or beads, depositing a volume of liquid that equates to about 27 wt % of the solvent absorption capacity of the silica support corresponds to a median radial penetration of about 10% of the average diameter of the particles. In that case, a global loading of 0.5 wt % of a noble metal by weight of the silica beads results in a coating (or shell) having an effective noble metal concentration of (0.5 wt % noble metal)/27.1%=1.8 wt % noble metal by weight of the shell of the silica bead. The noble metal local concentration in the shell of the silica bead is therefore increased by 3.6 times (1.8 wt %/0.5 wt %=3.6) compared to the case where the noble metal would be uniformly dispersed in the bead.

The liquid used in step (a) of the first aspect of the present invention contains a noble metal and a chelating agent and typically further contains a liquid vehicle in which the noble metal and the chelating agent are dispersed or dissolved, preferably dissolved. Most often, the liquid containing the noble metal and the chelating agent is a solution of the noble metal and the chelating agent, especially an aqueous solution. Examples of suitable liquid vehicles (also referred to as solvents) include, but are not limited to, water and other polar protic solvents, such as $C_1$-$C_4$ alkanols, for instance methanol, ethanol, n-propanol or isopropanol, and combinations thereof.

In the first aspect of the present invention, the noble metal is typically present in the noble metal-containing liquid used in step (a) in the form of a noble metal compound, preferably in the form of a precursor compound of said noble metal. Suitable precursor compounds are noble metal compounds which can be converted into the metallic noble metal. Conversion to metallic noble metal may, for example, involve a calcination step. The noble metal may be deposited on the surface of the silica support in any form, including salt forms, organo-metal compounds, metal oxides or complexes comprising noble metal atoms or ions. The noble metal is typically deposited onto the silica support as a salt, for example, in a suitable solvent, such as water or any other suitable liquid vehicle as defined above. Suitable noble metal salts include nitrate, nitrosyl nitrate, halide (typically bromide, chloride or iodide) and acetate salts, in particular nitrosyl nitrate. Ruthenium nitrosyl nitrate salts are especially preferred. Alternatively, the noble metal may be deposited onto the silica support by spraying the silica support with a nebulized liquid containing a noble metal oxide, for instance ruthenium oxide. In a specific embodiment, a compound, complex or salt of the noble metal, especially ruthenium, is dissolved in an aqueous solution, such as deionized water, and then treated with ultrasound to produce nebulized droplets which are then sprayed onto the silica support.

Advantageously, the noble metal is deposited on the silica support as a solution of a noble metal salt, more preferably, as a noble metal-chelating agent complex, for example, as a ruthenium-chelating agent complex. The formation of a noble metal-chelating agent complex typically inhibits undesired interactions among noble metal atoms, thus preventing noble metal particle agglomerations. The chelating agent advantageously acts as a dispersion aid.

The chelating agents for use in the methods of the invention include at least one and in particular from 1 to 6 nitrogen-containing functional groups selected from amine and imine functional groups (i.e., at least one amino and/or imino groups), such as from 1 to 6 secondary or tertiary amine functional groups. Preferably the chelating agent also includes at least one carboxylic acid and/or hydroxyl functional group, preferably from 1 to 6 carboxylic acid and/or hydroxyl functional groups, more preferably from 2 to 6 carboxylic acid and/or hydroxyl functional groups. In a particular embodiment, the chelating agent has from 2 to 20 carbon atoms, for example, from 4 to 15 carbon atoms. Advantageously, the chelating agent comprises at least one carboxylic acid and/or hydroxyl functional group as well as at least one nitrogen-containing functional group selected from amine and imine functional groups (preferably amine functional group), and has from 2 to 20 carbon atoms. Especially suitable chelating agents are amino alcohols and/or amino carboxylic acids comprising 1 to 6 carboxylic acid and/or hydroxyl functional groups, preferably at least 2 carboxylic acid and/or hydroxyl functional groups, more preferably 2 to 6 carboxylic acid and/or hydroxyl functional groups as well as 1 to 6 nitrogen-containing functional groups selected from amine and imine functional groups, especially 1 to 6 amine groups, more particularly 1 to 6 secondary or tertiary amine groups, and 2 to 20 carbon atoms, preferably from 2 to 15 carbon atoms, for example, from 2 to 10 carbon atoms. Advantageously, the chelating agent comprises 1 to 6 hydroxyl functional groups, preferably 2 to 6 hydroxyl functional groups, and 1 to 6 amine or imine functional groups, especially 1 to 6 amine functional groups, preferably 1 to 6 secondary or tertiary amine groups, and 2 to 20 carbon atoms, in particular from 2 to 15 carbon atoms, especially 2 to 10 carbon atoms. Suitable chelating agents include those described in U.S. Pat. No. 3,761,428 (Institute Francais du Petrole) (see col. 1, lines 51 to 64) and those described in US 2010/0133148 (ExxonMobil) (see paragraphs [0038] to [0042]), the disclosure of both of which is incorporated herein by reference. Preferred chelating agents for use in the methods of the invention include $C_2$ to $C_{20}$ amino alcohols, including dialkanolamines such as diethanolamine, dialkanoldiamines, and trialkanolamines, for instance triethanolamine (TEA). Other suitable chelating agents are amino carboxylic acids, including polyamino carboxylic acids, amino polycarboxylic acids such as nitrilotriacetic acid (NTA), and polyamino polycarboxylic acids such as ethylenediaminetetraacetic acid (EDTA), as well as polyamines, such as guanidine. Preferred chelating agents are TEA and EDTA, with TEA being especially preferred. Chelating agents comprising amine or imine functional groups have been found to form complexes with noble metal ions, such as Ru-TEA. Those complexes are advantageously anchored to the silica surface via the interactions with the hydroxyl groups (Si—OH) of the silica support. It has also been found that chelating agents comprising carboxylic acid or hydroxyl functional groups as well as at least one nitrogen-containing functional group selected from amine and imine groups form particularly strong interactions with the hydroxyl groups (Si—OH) of the silica support. Thus, chelating agents comprising amine and/or imine functional groups as well as carboxylic acid and/or hydroxyl functional groups have been found to be the most effective dispersion aids for noble metals. Typically, the noble metal is deposited on the silica support in the presence of an excess of chelating agent, for example, at least 5 molar equivalents of chelating agent, especially at least 10 molar equivalents of chelating agent, such as at least 15 molar equivalents of chelating agent.

The amount of noble metal utilized in the method of the first aspect present invention is such as to provide a concentration of noble metal in the catalyst of the second aspect of the present invention suitable for use in hydrogenating unsaturated hydrocarbons, preferably in hydrogenating phthalates. Typically, the concentration of noble metal, especially ruthenium, in a catalyst of the second aspect of the present invention is in the range of from about 0.1 wt % to about 5 wt % based on the total weight of the catalyst composition, preferably in the range of from about 0.1 wt % to about 2 wt %, and more preferably in the range of from about 0.2 wt % to about 1 wt %, especially from about 0.5 wt % to about 0.8 wt %, based on the total weight of the catalyst composition. Typically, the concentration of the noble metal precursor in the nebulized liquid is in the range of from about 0.01 Molar (M) to about 1.0 M, preferably in the range of from about 0.01 M to about 0.20 M, and more preferably in the range of from about 0.02 M to about 0.10 M, especially from about 0.03 M to about 0.08 M.

After depositing the noble metal on the silica support particles, the resulting noble metal-containing silica support is optionally subjected to a washing and/or drying step. The washing is typically done with water. The drying step typically includes a temperature generally in the range of from about 20° C. to about 200° C., preferably in the range of from about 50° C. to about 175° C., and more preferably in the range of from about 75° C. to about 150° C. The drying step may be performed under reduced pressure or under atmospheric pressure, in an inert atmosphere or in air, most often in air and under atmospheric pressure. The drying can also be promoted by passing a gas stream over or through the material to be dried, for example air or nitrogen. The drying time depends upon the desired degree of drying and the drying conditions and is preferably in the range of from 1 hour to 30 hours, preferably from 2 hours to 10 hours.

Further optionally, and alternatively or additionally to the drying step, the preparation of the silica-supported noble metal catalyst may comprise a calcination step (c) of the noble metal-containing silica support under a calcining condition, such as exposure to a high temperature, for example, in excess of about 200° C., preferably in excess of about 240° C., and more preferably in excess of about 260° C., for example, from about 200° C. to about 600° C., such as from about 240° C. to about 400° C. During calcining, substantially all volatile matter (e.g., water and carbonaceous materials) is removed. The optional calcination step (c) is usually conducted in air. The calcining time depends upon the amount of volatile matter to be removed and the calcining conditions and is preferably in the range of from 0.5 hours to 5 hours, preferably from 0.5 hours to 2 hours.

Advantageously, the silica-supported noble metal catalyst produced in the method of the invention is subjected to an activation step (d) in which the silica-supported noble metal catalyst is contacted with hydrogen gas. Typically the silica-supported noble metal catalyst is exposed to an atmosphere comprising at least 60% by volume hydrogen, for example at least 80% by volume hydrogen, especially at least 95% by volume hydrogen, for example, an atmosphere of essentially 100% hydrogen. Any gas present in addition to hydrogen is preferably an insert gas such as nitrogen. Typically the silica-supported noble metal catalyst is contacted with hydrogen gas at an elevated temperature such as a temperature of at least about 200° C., for example, a temperature of at least about 300° C., especially a temperature of at least about 400° C. For example, the silica-supported noble metal catalyst may be contacted with hydrogen gas at a temperature of from about 300° C. to about 650° C., such as from about 350° C. to about 500° C. Typically, the hydrogen pressure is slightly above ambient pressure, such as a pressure of from about 10 kPa gauge to about 100 kPa gauge, such as about 34 kPa gauge (5 psig), i.e., around 136 kPa absolute pressure. Typically, the silica-supported noble metal catalyst may be contacted with hydrogen gas for at least about 1 hour, such as for at least about 2 hours. Preferably, the silica-supported noble metal catalyst is contacted with hydrogen gas for no more than about 5 hours. Contacting of the silica-supported noble metal catalyst with hydrogen gas for about 2.5 hours has been found to be sufficient to fully activate the catalyst. Optional activation step (d) is advantageously performed after optional calcination step (c).

The activation step (d) may optionally be followed by a passivation step (e). Such a passivation step (e) can, for instance, be conducted by treating the catalyst briefly in an oxygen-containing gas, for example, air, but preferably with an inert gas mixture comprising from 0.1 to 10 volume percent of oxygen. It is also possible to use $CO_2$ or $CO_2/O_2$ mixtures. The passivation step may, for instance, be conducted at room temperature under atmospheric pressure for a few hours.

Advantageously, the silica-supported noble metal hydrogenation catalyst of the second aspect of the invention and/or the silica-supported noble metal hydrogenation catalyst produced by the method of the first aspect of the invention, has a hydrogen to noble metal chemisorption ratio, H/noble metal chemisorption ratio, preferably H/Ru chemisorption ratio, of at least about 0.50, especially at least about 0.60, preferably at least about 0.65. The H/noble metal chemisorption ratio is the molar ratio of hydrogen atoms absorbed on the catalyst for each noble atom and thus is a measure of the dispersion of the noble metal on the catalyst. A H/noble metal chemisorption ratio of 1 would indicate that 100% of noble metal atoms are bound to a hydrogen atom after chemisorption of hydrogen and are thus fully dispersed, such that each noble metal atom is accessible for hydrogen binding. A H/noble metal chemisorption ratio of 0.5 indicates that only 50% of the noble metal atoms are able to bind to hydrogen, the remainder being inaccessible. Suitable conventional volumetric chemisorption techniques which can be employed to measure hydrogen chemisorption of the catalysts of the invention are discussed in *Structure of Metallic Catalysts*, J. R. Anderson, Academic Press, 1975, chapter 6. The hydrogen to noble metal chemisorption ratio can, for example, be calculated by reduction of a sample of silica-supported noble metal catalyst that contains a known quantity of noble metal with hydrogen and determining the quantity of hydrogen absorbed onto the catalyst, for example, by extrapolation of the isothermal profile to zero hydrogen pressure, after reduction of the sample at 200° C. in hydrogen for 30 minutes.

Advantageously, the dispersity of the noble metal in the silica-supported noble metal hydrogenation catalyst of the second aspect of the invention and/or the silica-supported noble metal hydrogenation catalyst produced by the method of the first aspect of the invention, is at least 35%, such as at least 40% and especially greater than 50%, for example, at least 52%. In some embodiments, the dispersity may be greater than 60%, for example, at least 62%. Dispersity may be measured according to DIN 66136 1-3.

The silica-supported noble metal hydrogenation catalyst of the second aspect of the invention or the silica-supported noble metal hydrogenation catalyst produced by the method of the first aspect of the invention is especially suitable as a hydrogenation catalyst, in particular for the hydrogenation of unsaturated hydrocarbons, especially phthalates, for instance dimethyl phthalate, di-2-propylheptyl phthalate, di-2-ethyl-hexyl phthalate, dioctyl phthalate, or diisononyl-phthalate.

The surface area of the hydrogenation catalyst of the second aspect of the invention or produced in the method of the first aspect of the invention, as measured by the Brunauer, Emmett, Teller (BET) method, ASTM D1993, is usually at least about 80 $m^2/g$, preferably at least about 100 $m^2/g$, especially at least about 120 $m^2/g$. Typically, the surface area as measured by the BET method is 400 $m^2/g$ or less, for example, 300 $m^2/g$ or less, such as 2000 $m^2/g$ or less.

In one embodiment, the method of the first aspect of the invention is a method of producing a hydrogenation catalyst which comprises the steps of: (i) providing a silica support having an average diameter in the range of from about 0.8 mm to about 2.2 mm; (ii) providing an aqueous solution comprising a noble metal salt, especially a ruthenium salt, and a chelating agent that comprises at least one nitrogen-containing functional group selected from amine and imine functional groups as well as at least one carboxylic acid or hydroxyl functional group; (iii) nebulizing the solution; (iv) spraying the nebulized solution onto the silica support to produce a noble metal-containing silica support; (v) optionally drying the noble metal-containing silica support, (vi) calcining the noble metal-containing silica support to produce a silica-supported noble metal catalyst; and optionally (vii) activating the silica-supported noble metal catalyst by contacting the silica-supported noble metal catalyst with hydrogen gas. In an especially preferred embodiment, the catalyst is made by depositing a nebulized ruthenium-TEA aqueous solution onto a silica support.

In a further embodiment, the silica-supported noble metal catalyst of the second aspect of the invention is a silica-supported noble metal catalyst, especially ruthenium, hydrogenation catalyst, especially phthalate hydrogenation catalyst, consisting of particles having an average diameter of from about 0.7 mm to about 2.4 mm, that comprise from about 0.2 wt % to about 1 wt % noble metal and wherein the median radial penetration of noble metal into the silica support is no more than about 40% of the maximum dimension of said silica support. Advantageously, the silica-supported noble metal catalyst has a hydrogen to noble metal chemisorption ratio of at least about 0.50, especially at least about 0.60.

EXAMPLES OF THE INVENTION

The following examples illustrate the present invention. Numerous modifications and variations are possible and it is to be understood that within the scope of the appended claims, the invention may be practiced otherwise than as specifically described herein.

Examples 1 to 3—Preparation and Characterization of Ru/SiO$_2$ Rim-Structured Catalysts Silica beads, silica cylinder extrudates and silica quadrulobe extrudates were used as catalysts supports.

The average diameter (dry sieve analysis according to ASTM C136-96a or optical scanner imaging), the BET surface area (ASTM D1993), the pore volume (mercury porosimetry according to ASTM D4284-12), and the median pore size (mercury porosimetry according to ASTM D4284-12) of said silica beads and silica extrudates are listed in Table 1 below.

TABLE 1

| Ex. | SiO$_2$ Support | Average diameter (mm) | Surface Area (m$^2$/g) | Pore volume (ml/g) | Median pore size (nm) |
|---|---|---|---|---|---|
| 1 | SiO$_2$ beads | 2.0 | 205 | 1.11 | 17.4 |
| 2 | SiO$_2$ cylinder extrudates | 1.41 | 150 | 0.94 | 19.3 |
| 3 | SiO$_2$ quadrulobe extrudates | 1.27 | 334 | 0.86 | 8.8 |

The ruthenium precursor compound used in the catalyst preparation was ruthenium nitrosyl nitrate. The chelating agent was triethanolamine (TEA). 2.49 g of ruthenium nitrosyl nitrate solution containing 10.09 wt % Ru in distilled water was added to 7.42 g of triethanolamine (TEA). The solution was stirred until it was clear. The total solution volume prepared was about 10.0 ml. The concentration of Ru in the solution was 0.25 M and the TEA concentration was 4.97 M, giving a molar ratio of TEA to Ru of 20.

The ultrasonic nebulization apparatus employed in the catalyst preparation was manufactured by Sono-Tek at Milton, N.Y. The frequency of the ultrasonic nebulization used in the experiments was set at 60 kHz with 3.2 watts power. Under these conditions, the size of the droplets of the nebulized Ru-TEA solution was about 27 μm. The flow rate of the Ru-TEA aqueous solution through the nebulizer nozzle was controlled at 1 ml/min. The volume of Ru-TEA solution used for ultrasonic nebulization was about 27% of the absorption capacity of the silica supports, which gave about 10% radial penetration of Ru when the silica support was in the form of beads. 50 g of SiO$_2$ support (beads or extrudates) were used in the catalyst preparation.

After ultrasonic nebulization and spraying of the Ru-TEA solution onto the silica supports, the ruthenium-containing silica supports were dried in air at 100° C. for 12 hours and calcined in air at 275° C. for 1 hour, with a ramping rate of 5° C./min to produce a silica-supported ruthenium catalyst. The air flow rate inside the calciner was adjusted at 5 volume/volume catalyst/minute. The silica-supported ruthenium catalysts contained 0.5% Ru, with respect to the total weight of catalyst.

The Ru/SiO$_2$ catalysts prepared according to examples 1 to 4 were characterized by optical imaging using a Leica MZ16 stereomicroscope and DFC 480 mounted digital camera system. The camera system was connected to a PC running the software Image Pro Express, version 5.1, to acquire and analyze the images. The light source was supplied by a Leica KL1500 LCD cold light system using a 2-branch goose neck fiber-optic light guide. The SiO$_2$ catalysts were cut to produce a cross-sectional thickness of 1 mm or less.

Figure 1:
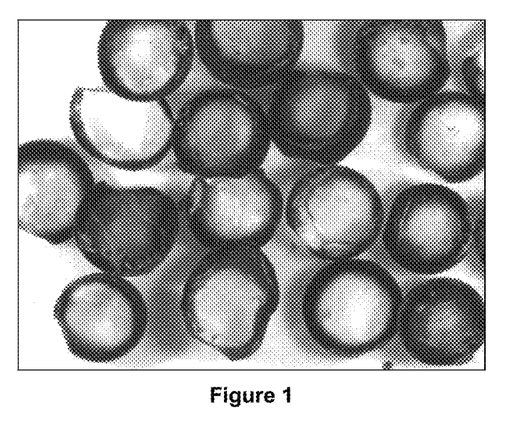
FIG. 1 shows a Ru egg-shell coating on $SiO_2$ beads.

FIG. 1 shows the optical microscopy image of the catalyst of Example 1 comprising 0.5 wt % Ru deposited as an egg-shelled coating on the SiO$_2$ beads (average diameter of 2.0 mm) with 10× magnification. The dark layers surrounding the silica beads are the rings of Ru metal coatings. The areas inside the silica beads are relatively clear and light colored, which indicates that there is little or no Ru metal in the center of the silica beads.

Figure 2:
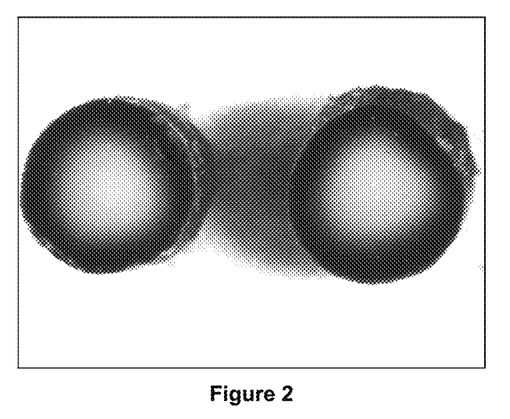
FIG. 2 shows a Ru egg-shell coating on $SiO_2$ cylinder extrudates.

FIG. 2 shows the optical microscopy image of the catalyst of Example 2 comprising 0.5 wt % Ru deposited as an egg-shell coating on the SiO$_2$ cylinder extrudates (average diameter 1.41 mm or 1/18 inch) with 25× magnification. The dark Ru rings surrounding the silica extrudates show more than 10% of radial Ru penetration into the silica extrudates in the case of cylinders. The calcination accelerates the Ru metal penetration to the center of the silica extrudates. The Ru rings are relatively thick compared to Ru coating on silica beads. The light colored areas inside the silica extrudates indicate that the Ru concentrations are low in the center of silica cylinder extrudates.

Figure 3:
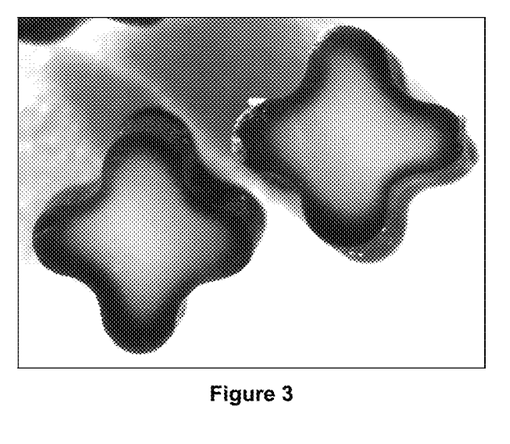
FIG. 3 shows a Ru egg-shell coating on $SiO_2$ quadrulobe extrudates.

FIG. 3 shows the optical microscopy image of the catalyst of Example 3 comprising 0.5 wt % Ru deposited as an egg-shell coating on the SiO$_2$ quadrulobe extrudates (average diameter 1.27 mm or 1/20 inch) with 32× magnification. The dark rings surrounding the silica quadrulobe extrudates are thinner than the Ru rings on the silica cylinder extrudates. The Ru rings are relatively uniform in thickness. Again, the light colored areas inside the silica extrudates indicate that the Ru concentrations are low in the center of silica cylinder extrudates.

Example 4—Preparation of Ru/SiO$_2$ Catalyst by Impregnation (Comparative)

A Ru/SiO$_2$ catalyst was prepared by incipient wetness impregnation of the SiO$_2$ cylinder extrudates used in Example 2, with the volume of the impregnation solution used being about 95% of the solution absorption capacity of the silica support. 8.37 g of ruthenium nitrosyl nitrate solution containing 1.5 wt % Ru was added to 3.73 g of triethanolamine (TEA). 10 g of water was added to the mixture of Ru-TEA. The solution was stirred until it was clear. The total solution volume prepared was about 23.8 ml. The concentration of Ru in the solution was 0.05 M and TEA was 1.05 M. The molar ratio of TEA to Ru was 21. 25 g of SiO$_2$ cylinder extrudates were used in the catalyst preparation.

After impregnation of the silica support with the Ru/chelating agent solution, the ruthenium-containing silica supports were dried in air at 100° C. for 12 hours and calcined in air at 275° C. for 1 hour with a ramping rate of 5° C./min to produce a silica-supported ruthenium catalyst. The air flow rate inside the calciner was adjusted at 5 volume/volume catalyst/minute. The silica-supported ruthenium catalyst contained 0.5% Ru, with respect to the total weight of catalyst.

As the catalyst was prepared by incipient wetness impregnation with a volume of impregnation solution of about 95% of the solution absorption capacity of the silica support, the Ru was mostly homogeneously dispersed through the catalyst support, i.e., not in the form of an egg-shell structure.

Example 5—Activation of the Ru/SiO$_2$ Catalysts by Reduction and Passivation

The Ru/SiO$_2$ samples of Examples 1 to 4 were placed in a reduction reactor and the temperature was ramped from room temperature to 425° C. at 5° C./min rate. The Ru/SiO$_2$ samples were reduced at 425° C. for 2.5 hours with 100% hydrogen. The hydrogen pressure was 34 kPa gauge (5 psig) adjusted by backpressure regulator plus atmospheric pressure. The reduced catalysts were allowed to cool down to room temperature in a H$_2$ flow. When the temperature of the reactor reached room temperature, the H$_2$ flow was replaced with a mixture of 1% air balanced with N$_2$. The catalyst passivation was carried out at room temperature for 2 hours. The gas flow of 1% air/N$_2$ then was adjusted at 5 volume/volume catalyst/minute.

Example 7—Benzene Hydrogenation Activity

The benzene hydrogenation activity (BHA) of the egg-shell catalysts of inventive Example 2 and Comparative Example 4 were compared.

The catalysts were reduced at 350° C. in H$_2$ for 1 hour prior to measuring the benzene hydrogenation activity (BHA). The BHA was defined as mole of benzene converted/mole of metal/hour. The BHA tests were carried out at 50° C., 75° C., 100° C. and 125° C. The BHA activity was the best fit value of the activities at these four different temperatures.

The BHA activity as well as the BET surface area (ASTM D1993), the pore volume (ASTM D4284-12) and the pore size (ASTM D4284-12) of the catalysts of Examples 2 and 4 are summarized in Table 2 below.

TABLE 2

| Ex. | Ru dispersion | BET surface area (m$^2$/g) | Pore Volume (ml/g) | Pore Size (nm) | BHA act. (mol Bz/ mol Ru/h) |
| --- | --- | --- | --- | --- | --- |
| 2 | Egg-shell | 150 | 0.94 | 19.3 | 720 |
| 4 | Homogeneous | 146 | 0.77 | 15.7 | 250 |

It can be seen from Table 2 that the egg-shell or rim structured catalyst of Example 2 shows a BHA that is 2.88 times higher than the BHA of the homogeneous catalyst of Comparative Example 4.

Without being bound by any theory, it is believed that, for a same global Ru metal loading of the catalyst (0.5 wt % in both Example. 2 and 4), the Ru concentration is much higher at the surface of a rim-structured catalyst than at the surface of a homogenously impregnated catalyst. As illustrated by the Examples above, this translates into a higher catalytic activity for benzene hydrogenation.

As other Comparative Examples, the rim-structured Catalyst A of Example 1.1 of US 2012/0296111, that contains 0.34 wt % Ru by weight of the catalyst, hydrogenates 0.064 moles of benzene in four hours (Example 2.1). This equates to a BHA of 140 mol/mol Ru/hour. Said rim-structured Catalyst A (Example 2.1) shows a small increase of benzene conversion rate when compared to Catalyst B (Comp. Example 1.2) that has a much greater penetration depth: Catalyst A provides 100% benzene conversion over 4 hours (Example 2.1) compared to 99.2% benzene conversation for catalyst B (Comp. Example 2.2). Similarly, the activity for phthalate hydrogenation of catalyst A is 97.7% compared to 97.2% for Comparative Catalyst B (Example 2.5 and 2.6).

These examples demonstrate that the method by which a rim-structured catalyst is produced has a substantial effect on the properties of the resulting catalyst. In particular, it has been shown that a catalyst prepared by the method of the present invention in which a noble metal is deposited on a silica support by spraying a nebulized liquid containing a noble metal precursor and a chelating agent has superior activity compared to a rim-structured catalyst prepared using previously known techniques. Without wishing to be bound to any theory, it is believed that the substantially higher activity of the catalyst of the present invention compared to that of US 2012/0296111 is due to superior dispersion of the metal at the surface of the silica support, which achieved using the method of the present invention.

The present invention has been described and illustrated by reference to particular embodiments. Those of ordinary skill in the art will appreciate that the invention lends itself to variations not necessarily illustrated herein. For this reason, then, reference should be made solely to the appended claims for purposes of determining the true scope of the present invention.

The invention claimed is:

1. A method for the preparation of a silica-supported noble metal hydrogenation catalyst having a radial penetration of the noble metal into silica particles of no more than about 40% of the average diameter of the silica particles in the range from about 0.7 mm to about 2.4 mm, the method comprising the steps of:
   (a) nebulizing a liquid containing a noble metal and a chelating agent to form a nebulized liquid, wherein the chelating agent comprises at least one nitrogen-containing functional group selected from the group consisting of amine and imine functional groups; and
   (b) contacting the nebulized liquid of step (a) with the silica particles to produce the silica-supported noble metal hydrogenation catalyst.

2. The method of claim 1, wherein the noble metal is selected from the group consisting of ruthenium, rhodium, palladium, platinum, and mixtures thereof.

3. The method of claim 1, wherein the nebulized liquid is in the form of a solution and wherein the noble metal is in the form of a noble metal salt.

4. The method of claim 3, wherein the noble metal salt is a nitrosyl nitrate salt.

5. The method of claim 3, wherein, in step (b), the silica particles are sprayed with a volume of the solution of the nebulized liquid corresponding to from about 20% to about 35% of the solvent absorption capacity of the silica-supported noble metal hydrogenation catalyst.

6. The method claim 1, wherein the chelating agent further comprises at least one carboxylic acid or hydroxyl functional group.

7. The method of claim 6, wherein the chelating agent has from 1 to 6 carboxylic acid or hydroxyl functional groups.

8. The method of claim 1, wherein the chelating agent has from 2 to 20 carbon atoms.

9. The method of claim 1, wherein the chelating agent has from 1 to 6 nitrogen-containing functional groups selected from the group consisting of amine and imine groups.

10. The method of claim 1, wherein the chelating agent is triethanolamine.

11. The method of claim 1, wherein the silica particles used in step (b) have an average diameter of no more than about 2.4 mm.

12. The method of claim 1, wherein the liquid containing the noble metal and the chelating agent is nebulized using ultrasound.

13. The method of claim 1, wherein the nebulized liquid containing the noble metal and the chelating agent has an average droplet size of from about 3 μm to about 40 μm.

14. The method of claim 1, wherein the method further comprises the step (c) of calcining the silica-supported noble metal hydrogenation catalyst produced in step (b).

15. The method of claim 14, further comprising the step (d) of contacting the silica-supported noble metal hydrogenation catalyst produced in step (b) or step (c) with hydrogen gas to form an activated silica-supported noble metal hydrogenation catalyst.

16. A silica-supported noble metal hydrogenation catalyst comprising a noble metal dispersed on silica particles and having a radial penetration of the noble metal into the silica particles of no more than about 40% of the average diameter of the silica particles in the range from about 0.7 mm to about 2.4 mm, the silica-supported noble metal hydrogenation catalyst prepared according to the method of claim 1.

17. The silica-supported noble metal hydrogenation catalyst of claim 16, wherein the silica-supported noble metal hydrogenation catalyst comprising from about 0.2 wt % to about 1.0 wt % of noble metal.

18. The silica-supported noble metal hydrogenation catalyst of claim 16, wherein the noble metal is ruthenium.

19. The silica-supported noble metal hydrogenation catalyst of claim 16, wherein the chelating agent is triethanolamine.

20. A method of hydrogenating an unsaturated hydrocarbon, comprising the step of contacting an unsaturated hydrocarbon with hydrogen gas in the presence of the silica-supported noble metal hydrogenation catalyst of claim 16.

21. The method of claim 20, wherein the unsaturated hydrocarbon is a phthalate.

* * * * *